(12) United States Patent
Ward

(10) Patent No.: US 9,238,571 B2
(45) Date of Patent: Jan. 19, 2016

(54) FORMULATIONS FOR C-MET KINASE INHIBITORS

(75) Inventor: Robert Ward, Hoddesdon (GB)

(73) Assignee: Merck Sharp & Dohme Limited, Hertfordshire (GB)

( * ) Notice: Subject to any disclaimer, the term of this patent is extended or adjusted under 35 U.S.C. 154(b) by 673 days.

(21) Appl. No.: 13/498,600

(22) PCT Filed: Sep. 21, 2010

(86) PCT No.: PCT/GB2010/051586
§ 371 (c)(1),
(2), (4) Date: Mar. 28, 2012

(87) PCT Pub. No.: WO2011/039527
PCT Pub. Date: Apr. 7, 2011

(65) Prior Publication Data
US 2012/0241402 A1  Sep. 27, 2012

Related U.S. Application Data

(60) Provisional application No. 61/247,046, filed on Sep. 30, 2009.

(51) Int. Cl.
*B66C 23/44* (2006.01)
*A61K 9/16* (2006.01)
*A61K 9/20* (2006.01)
(Continued)

(52) U.S. Cl.
CPC .............. *B66C 23/44* (2013.01); *A61K 9/1617* (2013.01); *A61K 9/1635* (2013.01); *A61K 9/2013* (2013.01); *A61K 9/2054* (2013.01);
(Continued)

(58) Field of Classification Search
CPC . A61K 31/44; A61K 31/444; A61K 2300/00; A61K 9/1617; A61K 9/1635; A61K 9/1694; A61K 9/2013; A61K 9/2034; C07D 213/06; C07D 221/16; C07D 227/02; C07D 231/12; C07D 401/00; C07D 401/14; C07C 59/40; C07C 59/265; C07C 229/24; C07C 307/32; B66C 23/44; B66C 23/76
USPC .................. 424/451, 457; 514/277, 290, 333; 546/79, 93, 256, 266
See application file for complete search history.

(56) References Cited

U.S. PATENT DOCUMENTS

| 7,550,478 B2 | 6/2009 | Dinsmore et al. |
| 8,101,603 B2 * | 1/2012 | Dinsmore et al. ......... 514/232.8 |

(Continued)

FOREIGN PATENT DOCUMENTS

| WO | H07-324032 | 12/1995 |
| WO | 03074032 A1 | 9/2003 |

(Continued)

OTHER PUBLICATIONS

Streubel et al., "pH-independent release of a weakly basic drug from water-insoluble and -soluble matrix tablets," 2000, Journal of Controlled Release 67:101-110.*

(Continued)

*Primary Examiner* — Jane C Oswecki
(74) *Attorney, Agent, or Firm* — Richard S. Parr; Laura M. Ginkel

(57) ABSTRACT

The instant invention relates to pharmaceutical compositions containing c-Met kinase inhibitors. Also disclosed are processes for making said pharmaceutical compositions.

7 Claims, 2 Drawing Sheets

(51) Int. Cl.
 A61K 31/444 (2006.01)
 B66C 23/76 (2006.01)
(52) U.S. Cl.
 CPC ............... *A61K31/444* (2013.01); *B66C 23/76* (2013.01); *A61K 9/1694* (2013.01)

(56) References Cited

U.S. PATENT DOCUMENTS

| | | | |
|---|---|---|---|
| 8,222,269 B2 * | 7/2012 | Dinsmore et al. | 514/290 |
| 2003/0195220 A1 | 10/2003 | Murakami et al. | |
| 2010/0166853 A1 * | 7/2010 | Bando et al. | 424/456 |

FOREIGN PATENT DOCUMENTS

| | | | | |
|---|---|---|---|---|
| WO | WO03074032 A1 * | 9/2003 | | A61K 9/16 |
| WO | 03084931 A1 | 10/2003 | | |
| WO | 2003084931 A1 | 10/2003 | | |
| WO | 2007002254 A2 | 1/2007 | | |
| WO | 2007002258 A2 | 1/2007 | | |
| WO | 2007022956 A2 | 3/2007 | | |
| WO | WO2007022956 A2 * | 3/2007 | | A61K 9/48 |
| WO | 2007050380 A2 | 5/2007 | | |
| WO | WO2008008310 A2 * | 1/2008 | | |
| WO | 2008008310 A2 | 6/2008 | | |

OTHER PUBLICATIONS

NCT00559182 on Aug. 31, 2008 available at: http://clinicaltrials.gov/archive/NCT00559182/2009_08_31.

Streubel, A, et al., Journal of Controlled Release, vol. 67, pp. 101-110 (2000), "pH-independent release of a weakly basic drug from water-insoluble and -soluble matrix tablets".

Christensen, JG et al., Cancer Letters, vol. 225, pp. 1-26 (2005), "c-Met as a target for human cancer and characterization of inhibitors for therapeutic intervention".

Christensen, JG et al., Cancer Research, vol. 63, (2003), pp. 7345-7355, "A selective small molecule inhibitor of c-Met kinase inhibits c-Met-dependent phenotypes in Vitro and exhibits cytoreductive antitumor activity in Vivo".

Sattler, M et al., Cancer Research, vol. 63, (2003), pp. 5462-5469, "A novel small molecule Met inhibitor induces apoptosis in cells transformed by the oncogenic TPR-MET tyrosine kinase".

Puri, N. et al., Cancer Research, vol. 67, No. 8, (2007), pp. 3529-3534, "A selective small molecule of c-Met, PHA665752, inhibits tumorigenicity and angiogenesis in mouse lung cancer xenografts".

Zou, Hy et al., Cancer Research, vol. 67, No. 9, (2007), pp. 4408-4417, "An orally available small-molecule inhibitor of c-Met, PF-2341066, exhibits cytoreductive antitumor efficacy through antiproliferative and antiangiogenic mechanisms".

Martens, T et al., Clinical Cancer Research, vol. 12, No. 20, (2006), pp. 6144-6152, "A novel one-armed anti-c-Met antibody inhibits glioblastoma growth in vivo".

Northrup, A et al., "Discovery of MK-8033, a highly specific c-Met/Ron dual inhibitor for the treatment of cancer", Poster #759, 101st American Association for Cancer Research Annual Meeting, Washington, DC, Apr. 17-21, 2010.

Baselga, J et al., Science, vol. 312, (2006), pp. 1175-1178, "Targeting tyrosine kinases in cancer: the second wave".

Cosmoglio, PM et al., Nature Reviews Drug Discovery, vol. 7, (2008), pp. 504-516, "Drug development of MET inhibitors: targeting oncogene addiction and expedience".

Gorocinova, K et al., Bulletin of the Chemists and Technologists of Macedonia, vol. 14, No. 1, (1995), pp. 23-30, "pH independent controlled release matrix tablets with weakly basic drugs as active substances. Effect of incorporated acids".

NCT00559182 on Nov. 15, 2007 available at: http://clinicaltrials.gov/archive/NCT00559182/2007_11_15.

NCT00559182 on Aug. 14, 2008 available at: http://clinicaltrials.gov/archive/NCT00559182/2008_08_14.

NCT00559182 on Aug. 31, 2009 available at: http://clinicaltrials.gov/archive/NCT00559182/2009_08_31.

Bhardwaj, V et al., Journal of Thoracic Oncology, vol. 7, No. 8, (2012), pp. 1211-1217, C-Met inhibitor MK-8003 radiosensitizes c-Met-expressing non-small-cell-lung cancer cells with radiation-induced c-Met-expression.

Mitra, A et al., Molecular Pharmaceutics, vol. 8, (2011), pp. 2216-2223, "Using absorption simulation and gastric pH modulated dog model for formulation development to overcome achlorhydria effect".

* cited by examiner

FORMULATIONS FOR C-MET KINASE INHIBITORS

BACKGROUND OF THE INVENTION

This invention relates to formulations of c-Met kinase inhibitors.

A variety of c-Met kinase inhibitors have been disclosed for the treatment of various disorders related to c-Met kinase functioning, including the treatment of cellular proliferative disorders. Such disorders include, but are not limited to, cancer, hyperplasias, restenosis, cardiac hypertrophy immune disorders and inflammation. Representative examples of c-Met kinase inhibitors include those disclosed International Publication WO2008/008310, which published on Jan. 17, 2008, to Merck & Co., Inc., which is hereby incorporated by reference in its entirety.

C-Met kinase inhibitors can be formulated for oral dosing as tablets, by using a direct compression, wet granulation, hot melt extrusion, spray drying and/or roller compaction method. Similarly, c-Met kinase inhibitors can be formulated for oral dosing as gelatin capsules, being a liquid in a soft capsule, or dry powder or semi-solid in a hard capsule. In addition, c-Met kinase inhibitors can be formulated for intravenous dosing.

The formulations of the instant invention have advantages over other formulations of c-Met kinase inhibitors. Many c-Met kinase inhibitors exhibit pH-dependent solubility through the pH range 1-7, having higher solubility in acidic pH. Based upon the sharp dependence of solubility on pH, it can be postulated that the performance of these formulations can vary based on variability in gastric pH. For example, recent data from clinical studies with Compound A indicated high variability in Compound A exposure among patients, with lower exposures in some patients who were concomitantly taking antacids (i.e. with high gastric pH). Exposure can vary due to many factors, including whether the inhibitor is taken with or without food. The formulations of the instant invention give in vivo exposures to the drug that are less sensitive to changes in gastric pH than other formulations. Hence while the formulations of the instant invention give a similarly high exposure to the drug at low gastric pH as other formulations, the formulations of the instant invention give a higher exposure to the drug at higher gastric pH than other formulations.

The use of acidulant as described in the instant invention is more efficacious than extemporaneous use of acidulant. For example, with the baseline of a simple formulation absent of acidulant, the improvement in drug solubilisation at high pH from the use of the instant invention is much greater than from coadministering an acidic beverage (e.g. cola).

SUMMARY OF THE INVENTION

The instant invention relates to pharmaceutical compositions containing c-Met kinase inhibitors. The pharmaceutical compositions of the instant invention give in vivo exposures to the drug that are less sensitive to changes in gastric pH than other formulations known in the art. Compared with other formulations known in the art, the formulations of the instant invention give a similarly high exposure to the drug at low gastric pH, but a higher exposure to the drug at higher gastric pH.

DETAILED DESCRIPTION OF THE INVENTION

Figure 1:
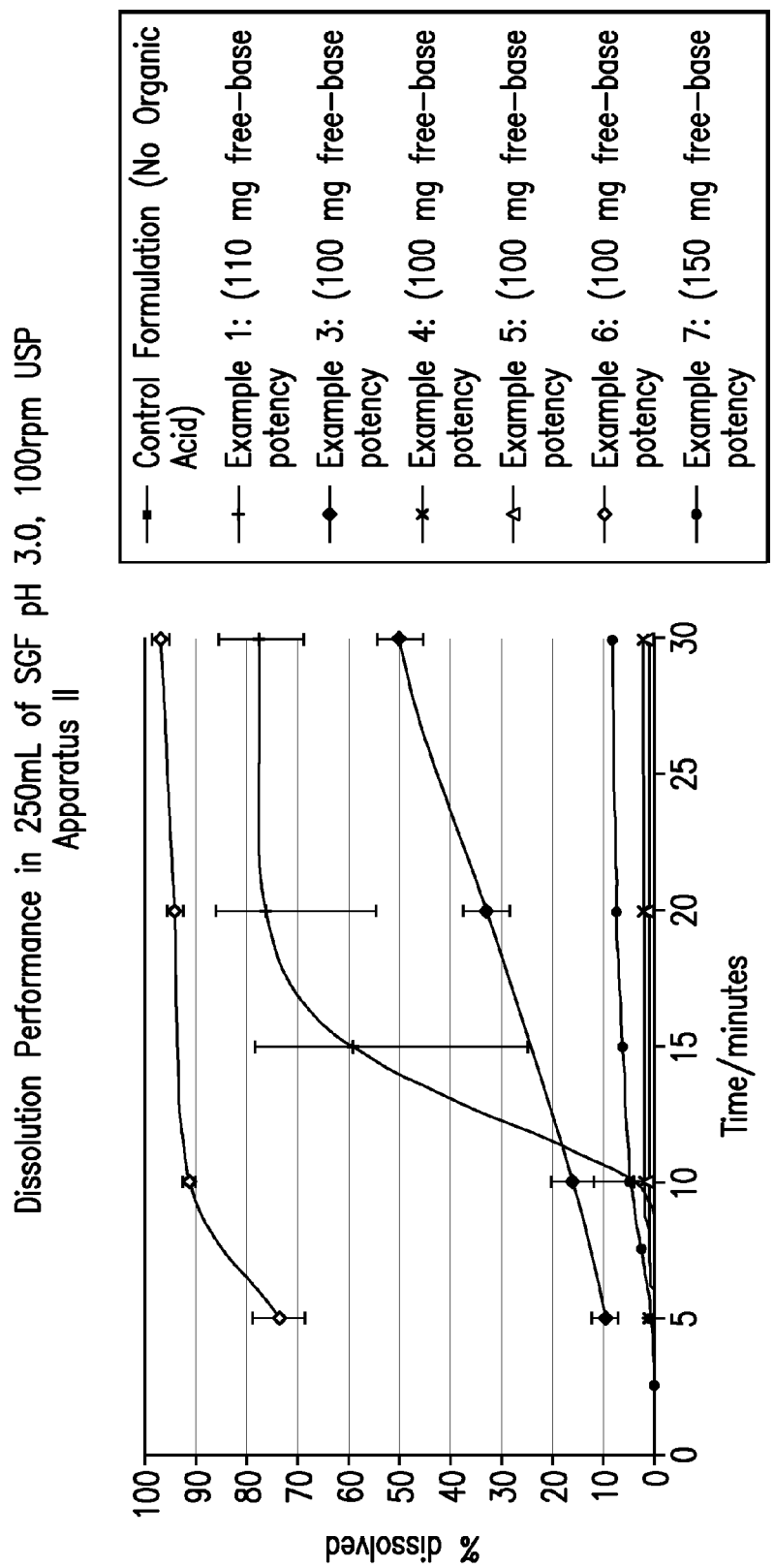
FIG. 1 describes the dissolution performance of the Compound A formulations described in Examples 1, 3, 4, 5, 6, 7 and a control formulation.

The instant invention relates to pharmaceutical compositions containing c-Met kinase inhibitors. The pharmaceutical compositions of the instant invention give in vivo exposures to the drug that are less sensitive to changes in gastric pH than other formulations known in the art. Compared with other formulations known in the art, the formulations of the instant invention give a similarly high exposure to the drug at low gastric pH, but a higher exposure to the drug at higher gastric pH.

A particularly effective c-Met kinase inhibitor is 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide,

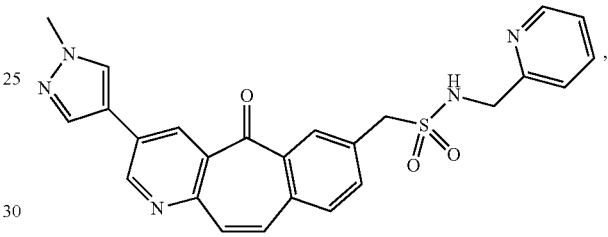

which can be prepared by procedures described in: International Publication WO2008/008310, which published on Jan. 17, 2008, to Merck & Co., Inc., which is hereby incorporated by reference in its entirety. This compound is also known as Compound A.

The invention contemplates the use of any pharmaceutically acceptable fillers/compression aids, disintegrants, super-disintegrants, lubricants, binders, surfactants, film coatings, and solvents. Examples of these components are set forth below and are described in more detail in the Handbook of Pharmaceutical Excipients, Second Edition, Ed. A. Wade and P. J. Weller, 1994, The Pharmaceutical Press, London, England.

The instant invention comprises a pharmaceutical composition comprising from 5% to 80% by weight of a c-Met kinase inhibitor, 5% to 80% by weight of an acidulant, 0% to 90% by weight of a diluent, 0 to 15% by weight of a disintegrant and from 0 to 5.0% by weight of a lubricant. In a class of the instant invention, is a pharmaceutical composition comprising from 30% to 35% by weight of a c-Met kinase inhibitor, 40% to 45% by weight of an acidulant, 20% to 25% by weight of a diluent, 1.0% to 5.0% by weight of a disintegrant and from 0.5% to 2.0% by weight of a lubricant.

In an embodiment of the invention, the weight ratio of the c-Met kinase inhibitor to acidulant is selected from within a range of 0.3 to 5.0.

In an embodiment of the invention, the c-Met kinase inhibitor is 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide (Compound A) or a pharmaceutically acceptable salt thereof.

In an embodiment of the invention, the acidulent is selected from the group consisting of acetic, adipic, benzenesulphonic, benzoic, caprylic, cinnamic, citric, ethanedisulphonic, tartaric, ascorbic, maleic, glutamic, lactic, oxalic, L-Aspartic, 2-hydroxyethanesulfonic, pamoic, malonic, gentisic, salicylic, fumaric, glucoheptoic, gluconic, glucuronic, hippuric, lactobionic, laurylsulfuric, malic, malonic, mandelic, methanesulphonic, propionic, stearic, toluenesulphonic, undecylenic, camphorsulfonic and oleic acid. In a class of the invention, the acidulent is citric acid.

In an embodiment of the invention, the diluent is selected from the group consisting of microcrystalline cellulose, lactose, mannitol, calcium phosphate, calcium carbonate, magnesium carbonate, sucrose, glucose, sorbitol, calcium sulfate, powdered cellulose, silicified microcrystalline cellulose, cellulose acetate, compressible sugar, dextrates, dextrin, dextrose, ethylcelluose, fructose, glyceryl palmitostearate, kaolin, lactitol, magnesium carbonate, magnesium oxide, maltodextrin, maltose, medium-chain triglycerides, polydextrose, polymethacrylates, simethicone, sodium alginate, sodium chloride, tragacanth, trehalose, xylitol and starch. In a class of the invention, the diluent is microcrystalline cellulose.

In an embodiment of the invention, the disintegrant is selected from the group consisting of croscarmellose sodium, starch, crospovidone, sodium starch glycolate, calcium carbonate, sodium carbonate, magnesium carbonate, alginic acid, tribasic calcium phosphate, calcium carboxymethylcellulose, sodium carboxymethylcellulose, powdered cellulose, chitosan, colloidal silicon dioxide, guar gum, hydroxypropyl cellulose, magnesium aluminium silicate, methylcellulose, povidone, and sodium alginate. In a class of the invention, the disintegrant is croscarmellose sodium.

In an embodiment of the invention, the lubricant is selected from the group consisting of magnesium stearate, stearic acid, sodium stearyl fumerate, talc, calcium stearate, glycerin monostearate, glyceryl behenate, glyceryl palmitostearate, magnesium lauryl sulfate, medium chain triglycerides, poloxamer, sodium benzoate, sodium chloride, sodium lauryl sulfate and zinc stearate. In a class of the invention, the lubricant is magnesium stearate.

The instant invention further comprises a method of improving the absorption of a c-Met kinase inhibitor by administering a pharmaceutical composition comprising from 5% to 80% by weight of a c-Met kinase inhibitor, 5% to 80% by weight of an acidulant, 0% to 90% by weight of a diluent, 0 to 15% by weight of a disintegrant and from 0 to 5.0% by weight of a lubricant. In a class of the invention, the C-met kinase inhibitor is Compound A. In another class of the invention the acidulant is citric acid, the diluent is microcrystalline cellulose, the disintegrant is croscarmellose sodium and the lubricant is magnesium stearate.

The instant invention further comprises a method of improving the absorption of a c-Met kinase inhibitor by administering a pharmaceutical composition wherein the weight ratio of c-Met kinase inhibitor to acidulant is selected from within a range of 0.3 to 5.0. In a class of the invention, the C-met kinase inhibitor is Compound A and the acidulant is citric acid.

The instant invention further comprises a method of improving the dissolution performance and in vivo exposure of a formulation containing a c-Met kinase inhibitor by incorporating an acidulent into the formulation. The incorporation of the acidulent into the composition results in a greater dissolution performance and in vivo exposure corresponding to high gastric pH compared to having the same quantity of acidulent pre-dissolved in vitro or in vivo.

The pharmaceutical compositions of the present invention, including tablets and capsules, may also contain one or more additional formulation ingredients that may be selected from a wide variety of excipients known in the pharmaceutical formulation art. According to the desired properties of the composition, any number of ingredients may be selected, alone or in combination, based upon their known uses in preparing pharmaceutical compositions. Such ingredients include, but are not limited to, diluents, binders, compression aids, disintegrants, lubricants, glidants, stabilizers (such as dessicating amorphous silica), flavors, flavor enhancers, sweeteners, preservatives, colorants and coatings.

The term "tablet" as used herein is intended to encompass compressed pharmaceutical dosage formulations of all shapes and sizes, whether uncoated or coated. Substances which may be used for coating include hydroxypropylmethylcellulose, hydroxypropylcellulose, titanium dioxide, talc, sweeteners and colorants.

The term "capsule" as used herein is intended to encompass compressed pharmaceutical dosage formulations of all shapes and sizes, whether uncoated or coated. Substances which may be used for coating include hydroxypropylmethylcellulose, hydroxypropylcellulose, titanium dioxide, talc, sweeteners and colorants. Substances which may be used for coating include hydroxypropylmethylcellulose, hydroxypropylcellulose, titanium dioxide, talc, sweeteners and colorants.

The pharmaceutical compositions of the present invention are useful in the therapeutic or prophylactic treatment of disorders associated with c-Met kinase functioning, including the treatment of cellular proliferative disorders. Such disorders include, but are not limited to, cancer, hyperplasias, restenosis, cardiac hypertrophy immune disorders and inflammation.

The formulations of the instant invention ensure that the biological benefits of the c-met kinase inhibitor are experienced across the widest number of patients, including those with higher-than-normal gastric pH (e.g. those patients on gastric-pH modifying drugs such as proton pump inhibitors). The formulations of the instant invention should provide benefits in the presence of proton pump inhibitors, including, but not limited to, omeprazole, raberprazole, esomeprazole, lansoprazole and patoprazole; H-2 blockers, including, but not limited to, cimetidine, famotidine, nizatidine and ranitidine; and antacids, including, but not limited to, carafate, sodium bicarbonate, calcium carbonate, magnesium hydroxide and aluminum hydroxide. Additionally, the formulations of the instant invention are expected to reduce the variability in exposure that arises from natural inter-subject variations in gastric pH (not arising from pH modifying drugs).

The following examples are given for the purpose of illustrating the present invention and shall not be construed as being limitations on the scope of the invention.

| Ingredient | Unit Formula % w/w | Amount (g) |
| --- | --- | --- |
| Compound A HCl salt | 31.00 | 465.0 |
| Citric acid, anhydrous, fine powder | 41.94 | 629.1 |
| Microcrystalline cellulose, Compendial (Avicel PH101) | 23.06 | 345.9 |
| Croscarmellose sodium | 3.000 | 45.0 |
| Magnesium stearate, Compendial [Non-bovine] (Intragranular) | 0.5000 | 7.500 |
| Magnesium stearate, Compendial [Non-bovine] (Extragranular) | 0.5000 | 7.500 |
| % Total | 100.0 | 1500.0 |

The capsules (HPMC shells) were prepared by encapsulating granule produced as follows. The citric acid, Avicel PH101, croscarmellose sodium and Compound A are mixed together in a drum blender. The intra-granular portion of the magnesium stearate (deagglomerated using a fine screen) was added to the mixture, and the mixture was lubricated using a blender. The lubricated blend was dry granulated using a roller compactor with in-built mill and coarse screen(s). The resultant granule was lubricated by adding the extra-granular portion of the magnesium stearate (deagglomerated using a fine screen) and mixing using a blender.

| Ingredient | Unit Formula % w/w | Amount (g) |
|---|---|---|
| Composition of the final material: | | |
| Compound A free base | 15 | 0.825 |
| Citric acid, anhydrous, fine powder (intra-comelt) | 5 | 0.275 |
| Citric acid, anhydrous, fine powder (extra-comelt) | 15 | 0.825 |
| Copovidone (VA 64) | 30 | 1.65 |
| Microcrystalline cellulose (Avicel PH102) | 35 | 1.925 |
| % Total | 100.0 | 5.5 |
| Composition of the comelt intermediate: | | |
| Compound A free base | 30 | 7.5 |
| Citric acid, anhydrous, fine powder (intra-comelt) | 10 | 2.5 |
| Copovidone (VA 64) | 60 | 15 |
| % Total | 100.0 | 25 |

Compound A, the intra-comelt portion of citric acid, and the Kollidon VA64 were blended together in a glass bottle using a Turbula blender. The blend was manually fed into a 16 mm ThermoElectron extruder at Zone 7. Zones 2-8 were continuously cooled, while zones 9 and 10 were heated to a set point of 200° C. and a screw speed of 200 RPM. Extrudate emerging from the 3 mm circular orifice die were collected, air cooled, and subsequently milled using a Fitzmill set up with 0030 screen at 6500 RPM.

A sample of the comelt intermediate was then blended with the microcrystalline cellulose and the extra-comelt portion of citric acid in a glass bottle using a turbula blender. The lubricated blend was dry granulated by passing slugs (i.e. loose compacts made on a tablet press) through a coarse screen. The granular material was then filled into capsules.

| Ingredient | Unit Formula % w/w | Amount (g) |
|---|---|---|
| Compound A free base | 25.0% | 6.15 |
| Microcrystalline cellulose (Avicel PH101) | 24.2% | 5.953 |
| Citric Acid, Anhydrous, intra-granular | 17.8% | 4.38 |
| PVP (K29/32) | 3.6% | 0.8856 |
| Croscarmellose Sodium, intra-granular | 0.4% | 0.0984 |
| Magnesium Stearate, intra-granular | 0.5% | 0.123 |
| Citric Acid, Anhydrous, extra-granular | 25.0% | 6.149 |
| Croscarmellose Sodium, extra-granular | 3.0% | 0.738 |
| Magnesium Stearate, extra-granular | 0.5% | 0.123 |
| Total: | 100% | 24.6 |

The tablets were prepared with a suitable press by compressing granule, prepared as follows. The Compound A and PVP were mixed together in a blender together with the intra-granular portions of Avicel, citric acid and croscarmellose sodium. The intra-granular portion of magnesium stearate (deagglomerated using a fine screen) was added to the mixture, and the mixture was lubricated using a drum blender. The lubricated blend was dry granulated using a roller compactor with in-built mill and coarse screen(s). The resultant granule was lubricated by adding the extra-granular portion of the magnesium stearate (deagglomerated using a fine screen) and mixing using a blender.

| Ingredient | Unit Formula % w/w | Amount (g) |
|---|---|---|
| Compound A HCl salt | 26.94 | 0.269 |
| Glutamic acid, anhydrous | 50.9 | 0.509 |
| Microcrystalline cellulose, Compendial (Avicel PH101) | 8.88 | 0.089 |
| Lactose Monohydrate | 8.88 | 0.089 |
| Croscarmellose sodium | 3.4 | 0.034 |
| Magnesium stearate, Compendial [Non-bovine] (Intragranular) | 0.5000 | 0.005 |
| Magnesium stearate, Compendial [Non-bovine] (Extragranular) | 0.5000 | 0.005 |
| % Total | 100.0 | 1.000 |

The capsules (hard gelatin shells) were prepared by encapsulating granule produced as follows. The glutamic acid, Avicel PH101, lactose monohydrate, croscarmellose sodium and Compound A are mixed together in a drum blender. The intra-granular portion of the magnesium stearate (deagglomerated using a fine screen) was added to the mixture, and the mixture was lubricated using a blender. The lubricated blend was dry granulated by passing slugs (i.e. loose compacts made on a tablet press) through a coarse screen. The resultant granule was lubricated by adding the extra-granular portion of the magnesium stearate (deagglomerated using a screen) and mixing using a blender.

| Ingredient | Unit Formula % w/w | Amount (g) |
|---|---|---|
| Compound A HCl salt | 25.0 | 0.400 |
| Ascorbic acid | 15.0 | 0.240 |
| PVP K29/32 | 5.0 | 0.080 |
| Microcrystalline cellulose, Compendial (Avicel PH101) | 22.0 | 0.352 |
| Lactose Monohydrate | 15.0 | 0.352 |
| Croscarmellose sodium | 10 | 0.160 |
| Magnesium stearate, Compendial [Non-bovine] (Intragranular) | 0.5000 | 0.008 |
| Magnesium stearate, Compendial [Non-bovine] (Extragranular) | 0.5000 | 0.008 |
| % Total | 100.0 | 1.600 |

The tablets were prepared using a tablet press by compressing granule produced as follows. The ascorbic acid, PVP, Avicel PH101, lactose monohydrate, croscarmellose sodium and Compound A are mixed together in a drum blender. The intra-granular portion of the magnesium stearate (deagglomerated using a fine screen) was added to the mixture, and the mixture was lubricated using a blender. The lubricated blend was dry granulated by passing slugs (i.e. loose compacts made on a tablet press) through a coarse screen. The resultant granule was lubricated by adding the extra-granular portion of the magnesium stearate (deagglomerated using a screen) and mixing using a blender.

| Ingredient | Unit Formula % w/w | Amount (g) |
| --- | --- | --- |
| Compound A HCl salt | 27.93 | 1.185 |
| Maleic acid | 31.89 | 1.353 |
| Microcrystalline cellulose, Compendial (Avicel PH101) | 17.8 | 0.755 |
| Lactose Monohydrate | 17.8 | 0.755 |
| Croscarmellose sodium | 3.53 | 0.150 |
| Magnesium stearate, Compendial [Non-bovine] (Intragranular) | 0.52 | 0.022 |
| Magnesium stearate, Compendial [Non-bovine] (Extragranular) | 0.52 | 0.022 |
| % Total | 100.0 | 4.242 |

The capsules (hard gelatin shells) were prepared by encapsulating granule produced as follows. The maleic acid, Avicel PH101, lactose monohydrate, croscarmellose sodium and Compound A are mixed together in a drum blender. The intra-granular portion of the magnesium stearate (deagglomerated using a fine screen) was added to the mixture, and the mixture was lubricated using a blender. The lubricated blend was dry granulated by passing slugs (i.e. loose compacts made on a tablet press) through a coarse screen. The resultant granule was lubricated by adding the extra-granular portion of the magnesium stearate (deagglomerated using a screen) and mixing using a blender.

| Ingredient | Unit Formula % w/w | Amount (g) |
| --- | --- | --- |
| Compound A HCl salt | 78.0 | 7.000 |
| Citric acid, anhydrous, fine powder | 16.0 | 1.436 |
| Sodium Lauryl Sulphate | 5.0 | 0.449 |
| Magnesium stearate, Compendial [Non-bovine] (Intragranular) | 0.5000 | 0.045 |
| Magnesium stearate, Compendial [Non-bovine] (Extragranular) | 0.5000 | 0.045 |
| % Total | 100.0 | 8.974 |

The capsules (hard gelatin shells) were prepared by encapsulating granule produced as follows. The citric acid, sodium lauryl sulphate and Compound A are mixed together in a drum blender. The intra-granular portion of the magnesium stearate (deagglomerated using a fine screen) was added to the mixture, and the mixture was lubricated using a blender. The lubricated blend was dry granulated using a roller compactor with in-built mill and coarse screen(s). The resultant granule was lubricated by adding the extra-granular portion of the magnesium stearate (deagglomerated using a fine screen) and mixing using a blender.

| Formulation | Dose (mg) | Pretreatment | $AUC_{0-24hr}$ ($\mu M * hr$) | $C_{max}$ ($\mu M$) | $T_{max}$ (hr) |
| --- | --- | --- | --- | --- | --- |
| Control Formulation (no organic acid) | 10 | Famotidine | 2.0 (1.2) | 0.2 (0.1) | 4 (0.5, 4) |
| Control Formulation (no organic acid) | 10 | Pentagastrin | 30.2 (6.5) | 4.3 (0.5) | 1.5 (1-4) |
| Example 1 | 10 | Famotidine | 18.4 (4.2) | 3.1 (0.6) | 2 (1-4) |
| Example 1 | 10 | Pentagastrin | 29.0 (3.8) | 5.8 (0.8) | 2 (1-2) |
| Example 2 | 10 | Famotidine | 20.5 (4.2) | 3.2 (0.7) | 2 (1-2) |
| Example 3 | 10 | Famotidine | 4.7 (1.5) | 0.6 (0.2) | 3 (1-4) |

Animal studies in high gastric pH (famotidine pretreated) beagle dogs were conducted to evaluate the formulations. In general, the formulations containing the citric acid (Examples 1 to 3) provided ~2-10 fold higher exposures compared to the formulation that does not contain citric acid. These data support the claim that the formulations containing citric acid gave a higher exposure to the drug under higher gastric pH conditions than other formulations known in the art. Animal studies in normal gastric pH (pentagastrin pretreated) beagle dogs show that the formulation with citric acid (Example 1) gave a similarly high exposure to the drug as compared to the control formulation with no citric acid.

Note that the Control Formulation referred to above comprised hard gelatin capsules filled with a simple blend of Compound A free base, lactose monohydrate and magnesium stearate (x, y and z mg/capsule respectively)

Example 9

In Vitro Dissolution of Compound A Formulations

In vitro Dissolution, using USP apparatus II.
Dissolution media: SGF pH3.0 to make 1 L dissolve 2 g of NaCl in 1 L of water and adjust the pH to 3.0 using concentrated Hydrochloric acid.
Dissolution vessel temperature: 37° C.
Paddle speed: 100 rpm
Sample timepoints: 5, 10, 20, 30 minutes with additional timepoints taken as needed.
Sampling volume: 1.5 mL
Filter: Gelman acrodisc 1 µm glass fibre
Diluent: 50/50 Acetonitrile/Water+0.02% TFA (mix 500 mL of Acetonitrile with 500 mL of water and add 200 µL of TFA)
Sample dilution: Take 250 µL of filtered sample and dilute with 250 µL of diluent.
HPLC Method for the Analysis of Dissolution Samples:
Column: Phenomenex Luna C18, 4.6 mm×50 mm, 3 µm
Mobile Phase A: Water+0.02% TFA
Mobile Phase B: Methanol
Elution mode: Isocratic (45% B)
Column temperature: 45° C.
Injection volume: 2 µL
Detector wavelength: 260 nm
Flow rate: 2 mL/min
Run time: 2 minutes From FIG. 1 it can be seen that the Examples 1 & 3-7, which are described in the instant invention, all give a higher extent of dissolution under relevant timescales (10-30 minutes) than the control formulation.

Note that the Control Formulation referred to in FIG. 1 comprises hard gelatin capsules filled with a simple blend of Compound A free base, lactose monohydrate and magnesium stearate (50, 91 and 1.42 mg/capsule respectively).

Example 10

Solubility Measurements of Compound A

Figure 2:
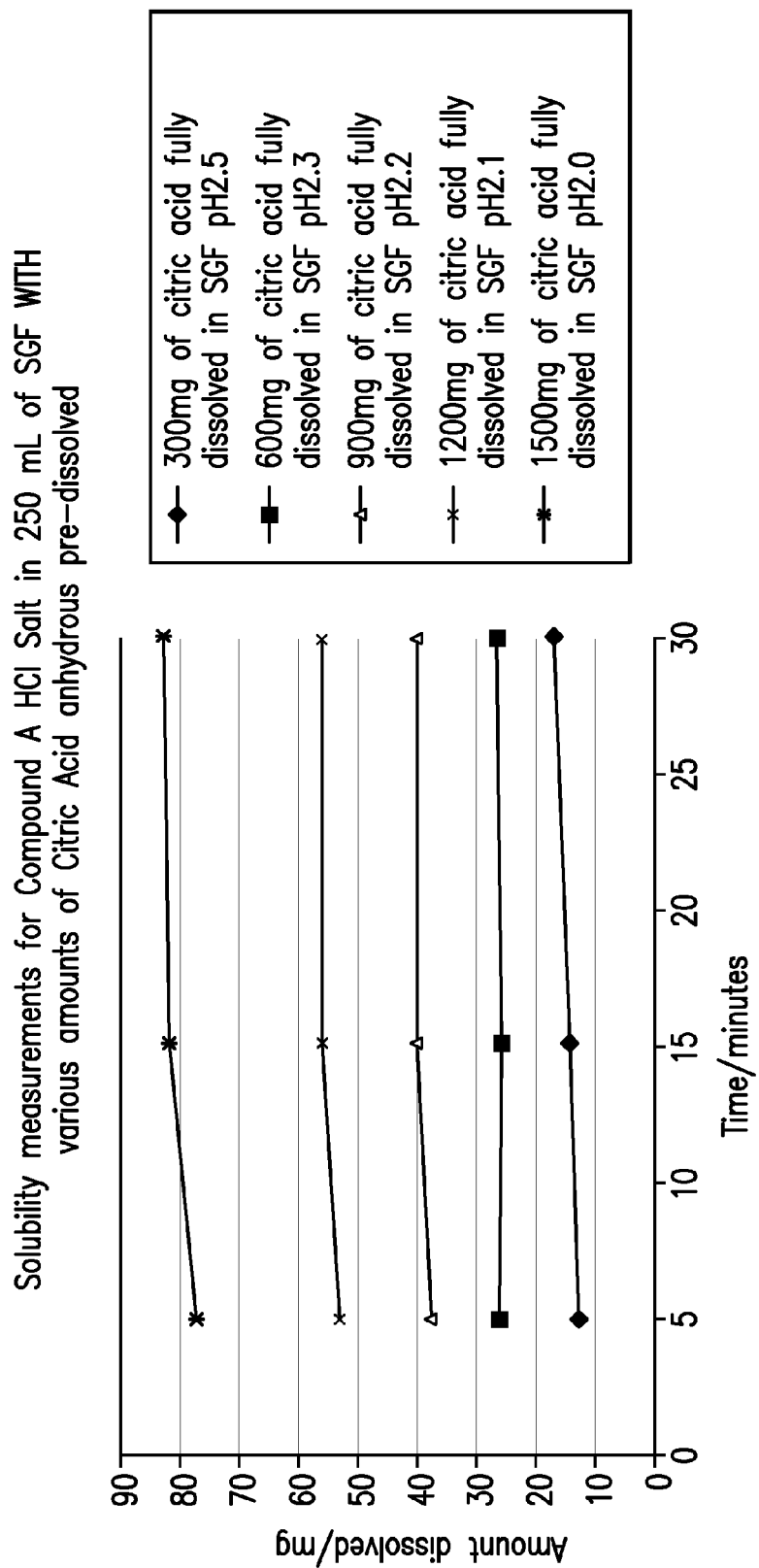
FIG. 2 describes the solubility measurements for Compound A HCl salt in 250 mL of SGF with various amounts of citric acid anhydrous pre-dissolved.

The graph in FIG. 2 shows that the maximum solubility achieved for Compound A when 300 mg of citric acid is fully dissolved in 250 mL of SGF pH 3.0 is approximately 15 mg. This would equate to a 14% dissolved for a 110 mg potency capsule. However in a Compound A HCl Salt 110 mg HPMC capsule containing 42% by weight citric acid anhydrous, a measured approximately 78% dissolved is achieved; hence the formulation is improving the dissolution performance. Within this formulation the amount of citric acid anhydrous available is 160.44 mg (Target fill weight for the capsule is 382.0 mg)

What is claimed is:

1. A pharmaceutical composition comprising from 30% to 35% by weight of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide or a pharmaceutically acceptable salt thereof, 40% to 45% by weight of an acidulant, 20% to 25% by weight of a diluent, 1.0% to 5.0% by weight of a disintegrant and from 0.5% to 2.0% by weight of a lubricant, wherein the weight ratio of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide to acidulant is selected from within a range of 0.3 to 5.0.

2. The pharmaceutical composition of claim 1 wherein the acidulent is selected from the group consisting of acetic, adipic, benzenesulphonic, benzoic, caprylic, cinnamic, citric, ethanedisulphonic, tartaric, ascorbic, maleic, glutamic, lactic, oxalic, L-Aspartic, 2-hydroxyethanesulfonic, pamoic, malonic, gentisic, salicylic, fumaric, glucoheptoic, gluconic, glucuronic, hippuric, lactobionic, laurylsulfuric, malic, malonic, mandelic, methanesulphonic, propionic, stearic, toluenesulphonic, undecylenic, camphorsulfonic and oleic acid.

3. The pharmaceutical composition of claim 1 wherein the diluent is selected from the group consisting of microcrystalline cellulose, lactose, mannitol, calcium phosphate, calcium carbonate, magnesium carbonate, sucrose, glucose, sorbitol, calcium sulfate, powdered cellulose, silicified microcrystalline cellulose, cellulose acetate, compressible sugar, dextrates, dextrin, dextrose, ethylcelluose, fructose, glyceryl palmitostearate, kaolin, lactitol, magnesium carbonate, magnesium oxide, maltodextrin, maltose, medium-chain triglycerides, polydextrose, polymethacrylates, simethicone, sodium alginate, sodium chloride, tragacanth, trehalose, xylitol and starch.

4. The pharmaceutical composition of claim 1 wherein the disintegrant is selected from the group consisting of croscarmellose sodium, starch, crospovidone, sodium starch glycolate, calcium carbonate, sodium carbonate, magnesium carbonate, alginic acid, tribasic calcium phosphate, calcium carboxymethylcellulose, sodium carboxymethylcellulose, powdered cellulose, chitosan, colloidal silicon dioxide, guar gum, hydroxypropyl cellulose, magnesium aluminium silicate, methylcellulose, povidone, and sodium alginate.

5. The pharmaceutical composition of claim 1 wherein the lubricant is selected from the group consisting of magnesium stearate, stearic acid, sodium stearyl fumerate, talc, calcium stearate, glycerin monostearate, glyceryl behenate, glyceryl palmitostearate, magnesium lauyl sulfate, medium chain triglycerides, poloxamer, sodium benzoate, sodium chloride, sodium lauryl sulfate and zinc stearate.

6. The pharmaceutical composition of claim 1 wherein the acidulant is citric acid, the diluent is microcrystalline cellulose, the disintegrant is croscarmellose sodium and the lubricant is magnesium stearate.

7. A method of improving the absorption of a c-Met kinase inhibitor by administering to a patient the pharmaceutical composition of claim 1.

* * * * *